United States Patent [19]
Juguin et al.

[11] Patent Number: 5,138,113
[45] Date of Patent: Aug. 11, 1992

[54] PROCESS FOR PRODUCING ALKYLAROMATIC HYDROCARBONS FROM NATURAL GAS

[75] Inventors: Bernard A. Juguin, Rueil Malmaison; Jean-Claude P. S. Collin, Vernouillet; Joseph Y. M. Larue, Chambourcy; Christian R. Busson, Dardilly, all of France

[73] Assignee: Institut Francais du Petrole, Rueil Malmaison, France

[21] Appl. No.: 618,423

[22] Filed: Nov. 27, 1990

[30] Foreign Application Priority Data

Nov. 28, 1989 [FR] France .............. 89 15767

[51] Int. Cl.$^5$ ............................................. C07C 2/66
[52] U.S. Cl. .................................. 585/322; 585/323; 585/446; 585/467; 585/943; 585/448; 585/450
[58] Field of Search ............ 585/322, 323, 446, 467, 585/943, 448, 450

[56] References Cited

U.S. PATENT DOCUMENTS

| | | | |
|---|---|---|---|
| 1,023,783 | 4/1912 | Knapp | 585/943 |
| 1,917,627 | 7/1933 | Wulff | 585/943 |
| 1,959,924 | 5/1934 | Mueller-Cunradi et al. | 585/943 |
| 2,343,870 | 3/1944 | Kaplan | 585/323 |
| 2,920,119 | 1/1960 | Egbert et al. | 585/323 |
| 4,447,664 | 5/1984 | Murchinson et al. | 585/323 |
| 4,571,442 | 2/1986 | Cosyns et al. | 585/261 |
| 4,812,536 | 3/1989 | De Simone et al. | 585/467 |
| 4,926,001 | 5/1990 | Alagy et al. | 585/500 |
| 4,952,546 | 8/1990 | Knuuttila et al. | 585/467 |

FOREIGN PATENT DOCUMENTS 0654684 12/1962 Canada .
1140159 1/1983 Canada .

Primary Examiner—Patrick P. Garvin
Assistant Examiner—E D. Irzinski
Attorney, Agent, or Firm—Millen, White & Zelano

[57] ABSTRACT

The invention relates to a process for producing alkylaromatic hydrocarbons from natural gas containing methane, characterized in that it comprises the following three successive stages:

1) thermal cracking of the natural gas with forming of hydrogen and $C_2^{30}$ hydrocarbons, particularly ethylene and acetylene,
2) separation of the $C_2+$ hydrocarbons, particularly of the ethylene and the acteylene, obtained at the end of stage 1), by cooled absorption in a solvent,
3) conversion of the $C_2+$ hydrocarbons from stage 2) into alkylaromatics.

The obtained alkylaromatics can be used as a base for premium gasoline.

11 Claims, 1 Drawing Sheet

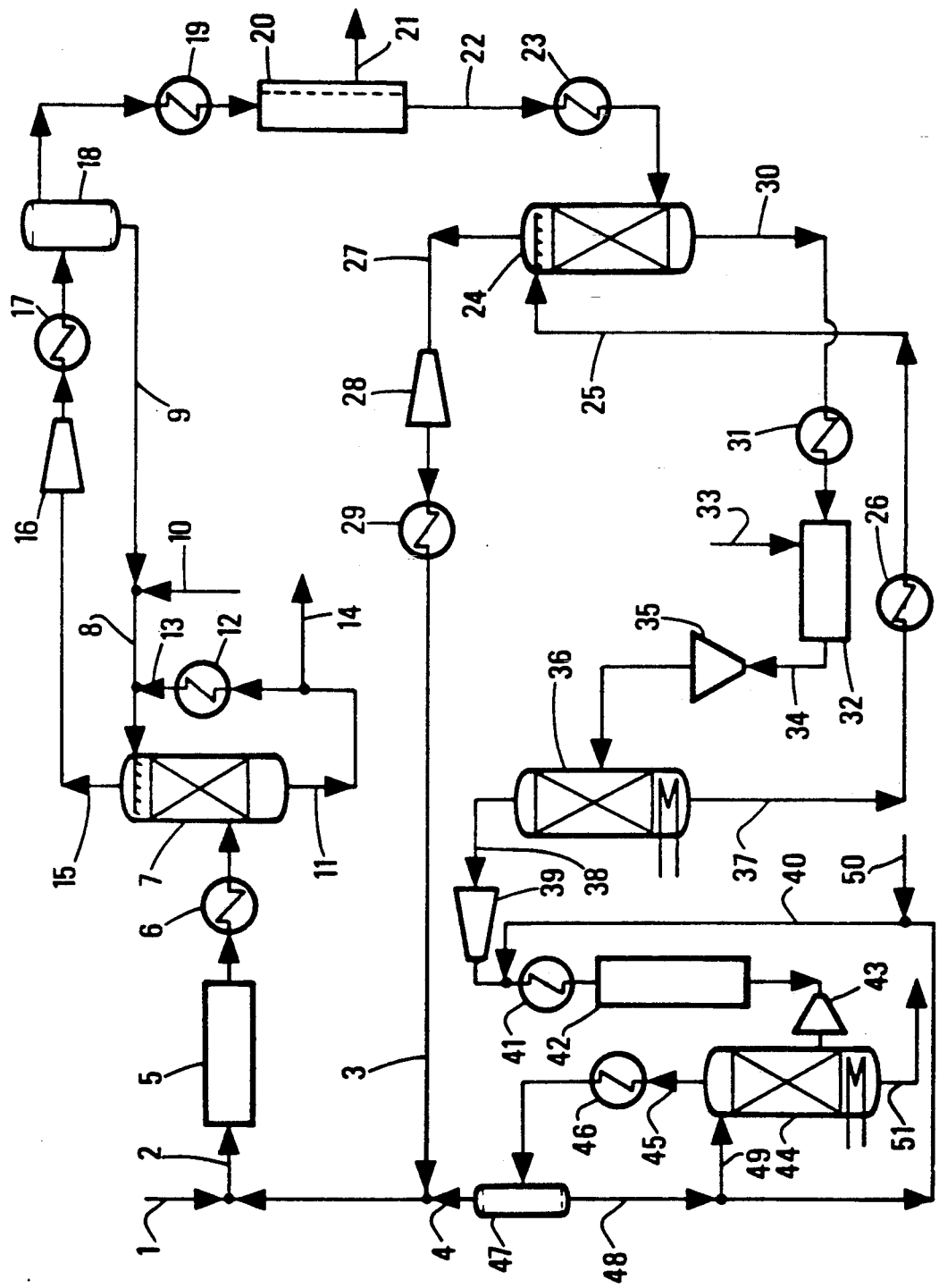

PROCESS FOR PRODUCING ALKYLAROMATIC HYDROCARBONS FROM NATURAL GAS

SUMMARY OF THE INVENTION

The present invention relates to a process for producing alkylaromatic hydrocarbons from natural gas.

Until now, the main processes for producing alkylaromatic hydrocarbons were reforming, steam cracking and alkylation. More recently, a new process for aromatizing light paraffins has been mentioned.

The process according to the invention comprises three main successive stages:

1) thermal cracking of the natural gas containing methane (for example 60 to 99% by volume) with forming of hydrogen and $C_2+$ hydrocarbons,
2) separation of the $C_2+$ hydrocarbons, obtained at the end of stage 1), by cooled absorption in a solvent such as toluene,
3) conversion of the $C_2+$ hydrocarbons from stage 2) into alkylaromatics.

Stage 1) of the thermal cracking of natural gas, more particularly methane, is performed in the presence of hydrogen, at a temperature generally ranging from 900° to 1,400° C., for example at about 1,200° C., preferably in a multichannel reactor made of silicon carbide through whose channels a heat-carrying fluid flows. This reaction, which notably generates hydrogen, $C_2+$ hydrocarbons (particularly ethylene and acetylene), heavy hydrocarbons ($C_7+$ hydrocarbons (except toluene)), is for example described in French patent applications 2,589,859, 2,596,046 and 2,600,329.

Stage 2) of separation of the $C_2+$ hydrocarbons advantageously comprises the following successive stages:

a) sending of the effluent from stage 1) into a quenching tower where said heavy hydrocarbons are at least partly absorbed in a heavy solvent, of the gas oil or oil type, and withdrawn at the bottom of the quenching tower, and where a gaseous phase is collected at the head of the quenching tower,
b) compression of the gaseous phase from stage a) in order to remove at least for the most part the remaining heavy products ($C_7+$ hydrocarbons (except toluene) and heavy solvent) from said gaseous phase, usually between 1 and 7 MPa, preferably between 3 and 5 MPa, for example at about 4 MPa,
c) separation of the excess hydrogen, generated by stage 1) and contained in the gaseous phase from stage b), by gaseous permeation,
d) cooled absorption of the $C_2+$ hydrocarbons contained in the gaseous phase from stage c), in a solvent such as toluene in order to substantially separate, on one hand, said $C_2+$ hydrocarbons (particularly ethylene and acetylene), in a liquid phase, and, on the other hand, the hydrogen and the methane, in a gaseous phase.

Phase 3) of conversion of the $C_2{}^{30}$ hydrocarbons into alkylaromatics advantageously comprises the following successive stages:

i) selective hydrogenation of the liquid phase comprising the $C_2+$ hydrocarbons (particularly ethylene and acetylene) in order to selectively convert the acetylene into ethylene,
ii) at least partial removal of the toluene contained in the effluent from stage i), said toluene being generally recycled towards stage d),
iii) alkylation of the toluene (which can be different from that which has been removed in stage ii)), by $C_2+$ hydrocarbons (particularly ethylene) contained in the mixture from stage ii).

Acetylene being a poison for catalysts used for the alkylation of toluene by ethylene, it is essential to convert it beforehand by selective hydrogenation (stage i)). This reaction of selective hydrogenation of acetylene is usually carried out in the presence of at least one catalyst arranged for example in the form of a fixed bed, said catalyst preferably consisting of at least one hydrogenizing metal, most often palladium, deposited on a substantially neutral support; such a catalyst is notably described in French patent application 2,552,078. The reaction temperature (stage i)) generally ranges from about 0° to 100° C., under a pressure ranging from about 0.1 to 10 MPa (the temperature preferably ranges from about 10° to 60° C. and the pressure, from about 1 to 6 MPa), with a liquid hydrocarbons flow rate (space velocity) ranging from about 2 to 20 volumes per volume of catalyst and per hour and with a molar ratio hydrogen/acetylene at the inlet of the hydrogenation reactor ranging from 0.5 to 5.

The reaction of alkylation of toluene, notably by ethylene (stage iii)), is generally achieved in the presence of at least one acid zeolitic catalyst arranged for example in the form of a fixed bed, usually at a temperature ranging from about 50° to 350° C. (preferably from about 150° to 300° C.), under a pressure ranging from 1 to 10 MPa (preferably from 2 to 7 MPa), with a liquid hydrocarbons flow rate (space velocity) ranging from about 0.2 to 5 volumes per volume of catalyst and per hour and with a molar ratio toluene/ethylene at the inlet of the alkylation reactor ranging from 0.5 to 20 (preferably from 2 to 15). The catalyst used in stage iii) is preferably based on a dealuminized mordenite with a total atomic ratio Si/Al ranging from 20 to 60; this catalyst is notably described in French patent applications 87/12,932, 88/14,099 and 88/17,164.

DETAILED DESCRIPTION OF THE INVENTION

A particular embodiment of the invention is described hereafter:

Natural gas essentially comprising methane is subjected to a thermal cracking reaction at high temperature in a multichannel reactor made of silicon carbide; at the outlet of said reactor, the effluent consists of hydrogen, methane, acetylene, ethylene, ethane, propene, butanes, benzene, toluene and $C_7$ hydrocarbons.

The effluent from the outlet of the thermal cracking reactor is cooled down to 200°–350° C. and injected into a quenching tower in which the heaviest hydrocarbons as well as the soots are absorbed in a heavy solvent of the gas oil or oil type. The liquid phase formed is pumped at the bottom of the quenching tower, cooled and recycled to the head; a pure solvent addition and a withdrawal are generally performed in order to avoid an accumulation of absorbed product.

The gaseous phase from the quenching tower is compressed between 3 and 5 MPa, for example at 4 MPa. Considering the rate of compression, the latter is preferably carried out in several stages with intermediate cooling. At the compressor outlet, the flow is brought back to a temperature close to the room temperature (15° to 25° C.), in order to condense the traces of heavy compounds (notably benzene and $C_7$ hydrocarbons), which are usually recycled towards the quenching tower.

The excess hydrogen generated by the cracking of the methane is separated by gaseous permeation. To that end, the flow is preheated in order to deviate from the dew point and then introduced into a permeator. The extracted hydrogen has a low pressure and is practically pure. This hydrogen flow can possibly be recycled in the further stage of selective hydrogenation of acetylene.

The fraction of $C_2+$ hydrocarbons is then separated from the hydrogen and the non converted methane (which are recycled to the thermal cracking reactor) by absorption. This operation is for example achieved by counterflow contact with cold toluene. The necessity of a high $C_2+$ recovery rate (generally higher than 97%) most often imposes operating conditions with a high pressure (for example about 4 MPa), a low temperature (for example about $-40°$ C.) and a solvent rate usually higher than 1. The liquid phase from the cooled absorption stage, which also contains a proportion of methane co-absorbed in the solvent, is sent in its entirety to the sagate of selective hydrogenation of acetylene.

The aqueous phase coming out at the head of the cooled absorption unit is expanded in a turbine. The cold produced thereby allows to ensure the total cooling that is necessary for the absorption. The mechanical work of expansion is recovered at the level of the compressors. The expanded flow is generally recycled to the thermal cracking reactor.

The liquid phase from the cooled absorption stage is then subjected to a selective hydrogenation the aim of which is to selectively convert the acetylene into ethylene. The operation is generally carried out with excess hydrogen (for example from 10 to 35%) in relation to the stoichiometry. The hydrogen can either come from the permeator (which causes an additional compression), or from the mixture of hydrogen and methane from the cooled absorption stage.

The amount of toluene contained in the flow from the selective hydrogenation stage is generally an excess amount for the alkylation stage. As a matter of fact, the molar ratio toluene/ethylene is generally higher than 20, whereas a value ranging from 7 to 15 is preferably required for the alkylation reaction. Besides, a separation by distillation of the toluene and the alkyltoluenes planned after the alkylation would be costly, since the main constituent, that is to say toluene, should be withdrawn at the column head. It is therefore necessary to separate before the alkylation the toluene that is not essential for this stage. For this reason, at the end of the selective hydrogenation stage, the toluene is at least partly removed the mixture is expanded at low pressure and fractionated in a column; the toluene withdrawn at the bottom is generally recycled to the cooled absorption stage, the topping gas being repressured and sent to the alkylation stage.

At the compressor outlet, this topping gas containing the ethylene is mixed with excess toluene (generally 7 to 15 times the stoichiometry). The obtained mixture is heated up between about 240° and 300° C., and then sent into an alkylation reactor where the ethylene and at least part of the toluene are converted notably into ethyltoluene and polyethyltoluenes.

At the outlet of the alkylation reactor, the effluent comprising the alkyltoluenes and the excess toluene is expanded and the effluent is injected into a second distillation column. The flow coming out at the column head essentially consists of hydrogen, methane, ethane, butanes and toluene. This flow is cooled down, and then sent into a condenser. The residual gaseous fraction (essentially methane and hydrogen) coming out at the condenser head is generally recycled to the thermal cracking reactor. The liquid fraction withdrawn at the condenser bottom (essentially toluene) is partly injected as a reflux into the second distillation column and partly recycled upstream from the alkylation reactor with generally make-up toluene to compensate for the part converted into alkyltoluenes. The alkyltoluenes are collected at the bottom of the second distillation column and sent for example to the gasoline pool of a refinery.

BRIEF DESCRIPTION OF THE DRAWING

The attached Figure is a schematic flowsheet of a comprehensive embodiment of the invention.

The following example illustrates the invention without limiting the scope thereof.

EXAMPLE AND DETAILED DESCRIPTION OF THE DRAWING

It is illustrated by the sole figure.

A feedstock (2) consisting of a mixture of fresh natural gas (1), essentially comprising methane, of gas (3) from the head of absorber (24) and of gas (4) from the head of the condenser (47) is introduced into a thermal cracking section (5).

Said feedstock (2) shows the following composition (expressed in kilogram):

| | |
|---|---|
| hydrogen | 661 |
| methane | 4,988 |
| ethylene | 3 |
| ethane | 35 |
| n-butane | 34 |
| toluene | 2 |
| | 5,723 |

The feedstock is thus preheated at about 600° C. and then cracked in a multichannel pyrolysis zone made of silicon carbide. A heat-carrying fluid consisting of burner combustion fumes at about 1,400° C. is sent across the channels meant for this use at a flow rate such that the temperature of the effluent mixture at the pyrolysis outlet is about 1,200° C.; the residence time of the feedstock in this zone is about 300 milliseconds. After passing across a quenching zone (supplied with air as a coolant), the temperature of the gaseous effluent is about 250° C.

This gaseous effluent coming out of (5) has, after cooling down (6) to the room temperature, the following composition (expressed in kilogram):

| | |
|---|---|
| hydrogen | 948 |
| methane | 3,680 |
| acetylene | 424 |
| ethylene | 339 |
| ethane | 16 |
| propene | 9 |
| n-butane | 34 |
| benzene | 190 |
| toluene | 6 |
| $C_7$ hydrocarbons | 77 |
| | 5,723 |

This corresponds to a conversion rate per pass of methane of about 26.2%.

These 5,723 kg of gaseous effluent are then sent into a quenching tower (7), at the same time as 1,112 kg of a heavy solvent comprising recycled solvent (9) and fresh make-up solvent (10). The composition of these 1,112 kg is the following:

| | | |
|---|---|---|
| hydrogen | 0.02 | |
| methane | 1.12 | |
| acetylene | 0.52 | |
| ethylene | 0.28 | |
| n-butane | 0.58 | |
| benzene | 30.42 | |
| toluene | 2.76 | |
| $C_7$ hydrocarbons | 32.86 | |
| gas oil | 1043.80 | |
| | 1,112 | |

At the bottom of the quenching tower, 1,056 kg of heavy products which are cooled (12) and recycled (13) at the top of the quenching tower, after a possible addition of heavy solvent (10), are withdrawn. These 1,056 kg of heavy products have the following composition:

| | |
|---|---|
| methane | 0.16 |
| benzene | 4.68 |
| toluene | 0.92 |
| $C_7$ hydrocarbons | 67.84 |
| gas oil | 982.40 |
| | 1,056 |

A withdrawal (14) can possibly be carried out notably in order to avoid an accumulation of absorbed products.

At the head (15) of this quenching tower, 5,779 kg of gaseous phase with the following composition are collected:

| | |
|---|---|
| hydrogen | 948.02 |
| methane | 3680.96 |
| acetylene | 424.52 |
| ethylene | 339.28 |
| ethane | 16 |
| propene | 9 |
| n-butane | 34.58 |
| benzene | 215.74 |
| toluene | 7.84 |
| $C_7$ hydrocarbons | 42.02 |
| heavy solvent | 61.04 |
| | 5,779 |

This gaseous phase is then compressed at 4 MPa (16) and brought back to the room temperature (17); 130 kg of heavy products are thus condensed, separated (18) and recycled (9) towards the quenching tower (7). These 130 kg of heavy products have the following composition:

| | |
|---|---|
| hydrogen | 0.02 |
| methane | 0.96 |
| acetylene | 0.52 |
| ethylene | 0.28 |
| n-butane | 0.58 |
| benzene | 30.42 |
| toluene | 2.76 |
| $C_7$ hydrocarbons | 33.42 |
| heavy solvent | 61.04 |
| | 130 |

After the separation of these heavy products recycled to the quench, 5,649 kg of gas are preheated (19) in order to deviate from the dew point, and introduced into a permeator (20) in order to decrease the excess hydrogen generated by the thermal cracking of the methane. These 5,649 kg of gas have the following composition:

| | |
|---|---|
| hydrogen | 948 |
| methane | 3,680 |
| acetylene | 424 |
| ethylene | 339 |
| ethane | 16 |
| propene | 9 |
| n-butane | 34 |
| benzene | 185.32 |
| toluene | 5.08 |
| $C_7$ hydrocarbons | 8.60 |
| | 5,649 |

At the permeator outlet, on one hand, 288 kg of pure hydrogen (21) are collected, which can be utilized in another section of the refinery (for example partly in the further stage of selective hydrogenation of acetylene) and, on the other hand, 5,361 kg of gaseous effluent (22) are collected which, after cooling (23), are sent towards an absorber (24). This effluent has the following composition (expressed in kilogram):

| | |
|---|---|
| hydrogen | 660 |
| methane | 3,680 |
| acetylene | 424 |
| ethylene | 339 |
| ethane | 16 |
| propene | 9 |
| n-butane | 34 |
| benzene | 185.32 |
| toluene | 5.08 |
| $C_7$ hydrocarbons | 8.60 |
| | 5,361 |

In the absorber (24), the fraction of $C_2^+$ hydrocarbons is substantially separated from the hydrogen and the methane by counterflow contact with 68,120 kg of toluene (25) cooled (26) down to about $-40°$ C. and coming from the bottom (37) of the distillation column (36).

After the reaction, 3,158 kg of gas are collected at the head (27) of the absorber and expanded (28), reheated (29) and then recycled (3) towards the thermal cracking section (5). These 3,158 kg of gas have the following composition:

| | |
|---|---|
| hydrogen | 655 |
| methane | 2,498 |
| ethylene | 3 |
| toluene | 2 |
| | 3,158 |

At the bottom (30) of the absorber, 70,323 kg of liquid phase with the following composition are withdrawn:

| | |
|---|---|
| hydrogen | 5 |
| methane | 1,182 |
| acetylene | 424 |
| ethylene | 336 |
| ethane | 16 |
| propene | 9 |
| n-butane | 34 |

-continued

| | |
|---|---|
| benzene | 185.4 |
| toluene | 68,123 |
| C7 hydrocarbons | 8.6 |
| | 70,323 |

This liquid phase is then reheated (31) and sent towards the selective hydrogenation section (32), where, in the presence of a palladium-based catalyst, the acetylene is hydrogenated in the following operating conditions:

| | |
|---|---|
| temperature | 20° C. |
| pressure | 4 MPa |
| liquid hourly flow rate = 10 times the volume of the catalyst | |
| molar ratio hydrogen/acetylene = 1.2, that is to say that 34 kg of hydrogen are added (33). | |

At the outlet (34) of the selective hydrogenation section, 70,357 kg of an effluent with the following composition are collected:

| | |
|---|---|
| hydrogen | 6 |
| methane | 1,182 |
| acetylene | 17 |
| ethylene | 757 |
| ethane | 35 |
| propene | 9 |
| n-butane | 34 |
| benzene | 185.4 |
| toluene | 68,123 |
| C7 hydrocarbons | 8.6 |
| | 70,357 |

This effluent is then expanded (35) and sent into a first distillation column (36) to separate the toluene from the lighter hydrocarbons.

At the bottom (36) of this distillation column, 68,120 kg of toluene, that ar recycled to the absorber head (24), are withdrawn.

At the head (38) of this distillation column, 2,237 kg of gaseous phase with the following composition are collected:

| | |
|---|---|
| hydrogen | 6 |
| methane | 1,182 |
| acetylene | 17 |
| ethylene | 757 |
| ethane | 35 |
| propene | 9 |
| n-butane | 34 |
| benzene | 185.4 |
| toluene | 3 |
| C7 hydrocarbons | 8.6 |
| | 2,237 |

This gaseous phase is repressured (39) and mixed with 25,538 kg of toluene (40); the resulting mixture, after preheating (41), is sent into an alkylation reactor (42) where the olefin are converted into alkylaromatic hydrocarbons, in the presence of a dealuminized mordenite with a total atomic ratio Si/Al of about 35, in the following operating conditions:

| | |
|---|---|
| temperature | 270° C. |
| pressure | 4 MPa |
| liquid hourly flow rate = twice the volume of the catalyst | |

At the outlet of the alkylation rector, 27,775 kg of a product with the following composition are collected:

| | |
|---|---|
| hydrogen | 6 |
| methane | 1,182 |
| ethane | 35 |
| n-butane | 34 |
| benzene | 167 |
| toluene | 22,917 |
| C7 hydrocarbons | 9 |
| ethylbenzene | 25 |
| methylethylbenzenes | 3,031 |
| methyldiethylbenzenes | 329 |
| methylisopropylbenzenes | 40 |
| | 27,775 |

After expanding (43), this product is sent into a second distillation column (44).

The product coming out at the head of this distillation column is cooled (46) and then sent into a condenser (47).

At the head (4) of this condenser, 1,257 kg of gas with the following composition are collected:

| | |
|---|---|
| hydrogen | 6 |
| methane | 1,182 |
| ethane | 35 |
| n-butane | 34 |
| | 1,257 |

This gas is then recycled towards the thermal cracking section (5).

At the bottom (48) of this condenser, 23,084 kg of liquid phase are collected and partly recycled towards the head (49) of the second distillation column (44) to serve as a reflux and partly recycled upstream (40) from the alkylation reactor, after adding make-up toluene (50).

At the bottom (51) of the second distillation column (44), 3,434 kg of product with the following composition are collected:

| | |
|---|---|
| C7 hydrocarbons | 9 |
| ethylbenzene | 25 |
| methylethylbenzenes | 3,031 |
| methyldiethylbenzenes | 329 |
| methylisopropylbenzenes | 40 |
| | 3,434 |

These 3,434 kg are a good base for premium gasoline and can thus be sent to the gasoline pool of the refinery.

| ASTM distillation | |
|---|---|
| initial point | 99° C. |
| final point | 212° C. |
| octane numbers | |
| clear RON | 110 |
| clear MON | 101 |

We claim:

1. A process for producing alkylaromatic hydrocarbons from natural gas containing methane, comprising the following successive steps:

1) thermal cracking of the natural gas to form an effluent of hydrogen, $C_2^+$ hydrocarbons comprising ethylene and acetylene, and $C_7^+$ heavy hydrocarbons,
2) separation of said $C_2^+$ hydrocarbons from methane and hydrogen, by cooled absorption in toluene,
3) selectively hydrogenating the resultant toluene phase containing $C_2^+$ hydrocarbons to convert acetylene into ethylene; and
3) reacting resultant ethylene-enriched $C_2^+$ hydrocarbons from step 3) with toluene, in contact with a catalyst, to from an alkylated toluene.

2. A process according to claim 1, wherein step 1) is carried out in the presence of hydrogen, at a temperature ranging from 900° to 1,400° C., in a multichannel reactor made of silicon carbide, through which channels a heat-carrying fluid flows.

3. A process according to claim 1, wherein step 2) comprises the following successive substeps:
a) sending of the effluent from step 1) into a quenching tower where the heavy hydrocarbons are at least partly absorbed in a heavy solvent and withdrawn at the bottom of said quenching tower, and wherein a gaseous phase containing ethylene and acetylene is collected at the head of said quenching tower,
b) compression between 1 and 7 MPa of the gaseous phase from substep a), in order to at least partially remove remaining heavy products from said gaseous phase,
c) separation of excess hydrogen, generated by step 1) and contained in the gaseous phase from substep b), by gaseous permeation, and
d) cooled absorption of the $C_2^+$ hydrocarbons, comprising ethylene and acetylene, contained in the gaseous phase from step c), in toluene, in order to substantially separate said $C_2^+$ hydrocarbons comprising ethylene and acetylene, from the hydrogen and the methane.

4. A process according to claim 3, wherein the hydrogen and the methane separated in step d) are recycled to step 1).

5. A process according to claim 1, wherein steps 3 and 4 comprise the following successive substeps:
i) at least partial removal of the toluene contained in the effluent from step 3) and employing the resultant removed toluene in step 4).

6. A process according to claim 3, wherein the excess hydrogen separated by gaseous permeation in substep c) is recycled to substep i).

7. A process according to claim 5, wherein step i) is performed in the presence of at least one catalyst formed by at least one hydrogenizing metal.

8. A process according to claim 1, wherein step 4) is performed in the presence of at least one catalyst based on a dealuminized mordenite with a total atomic ratio Si/Al ranging from 20 to 60.

9. A process according to claim 1, wherein the toluene employed in step (2) is alkylated in step (4).

10. A process for producing alkylaromatic hydrocarbons from natural gas containing methane, comprising the following successive steps:
1) thermal cracking of the natural gas to form hydrogen and $C_2^+$ hydrocarbons comprising ethylene and acetylene;
2) subjecting said hydrogen and $C_2^+$ hydrocarbons from step (1) to cold absorption in toluene to separate said $C_2^+$ hydrocarbons from methane and hydrogen;
3) vaporizing a portion of said toluene from resulting effluent from step (2) and reacting resultant vaporized toluene with at least a portion of the $C_2^+$ hydrocarbons to form alkylated toluene.

11. A process according to claim 10, wherein prior to reacting said $C_2^+$ hydrocarbons with toluene, removing acetylene from said $C_2^+$ hydrocarbons, thereby resulting in an acetylene-depleted $C_2^+$ hydrocarbon fractions for the production of alkylated toluenes.

* * * * *